(12) United States Patent
Brasseur (10) Patent No.: US 7,595,197 B2
(45) Date of Patent: Sep. 29, 2009

(54) AUTOMATED SAMPLE ANALYSIS

(75) Inventor: Michael Brasseur, Fremont, CA (US)

(73) Assignee: Caliper Life Sciences, Inc., Mountain View, CA (US)

( * ) Notice: Subject to any disclaimer, the term of this patent is extended or adjusted under 35 U.S.C. 154(b) by 978 days.

(21) Appl. No.: 10/842,073

(22) Filed: May 10, 2004

(65) Prior Publication Data

US 2005/0003554 A1    Jan. 6, 2005

Related U.S. Application Data

(60) Provisional application No. 60/469,431, filed on May 9, 2003.

(51) Int. Cl.
G01N 21/76 (2006.01)
G01N 1/10 (2006.01)
G01N 33/00 (2006.01)
G01N 21/64 (2006.01)

(52) U.S. Cl. .......................... 436/172; 436/180; 422/52; 422/68.1; 422/82.07; 422/82.08; 435/287.2

(58) Field of Classification Search ....................... None
See application file for complete search history.

(56) References Cited

U.S. PATENT DOCUMENTS 5,948,684 A * 9/1999 Weigl et al. .................... 436/52

2001/0052460 A1   12/2001 Chien et al.
2002/0487687      4/2002 Nikiforov

FOREIGN PATENT DOCUMENTS

WO    WO 98/56956 A1   12/1998

OTHER PUBLICATIONS

U.S. Appl. No. 09/645,104, filed Aug. 23, 2000, Kopf-Sill, et al.

* cited by examiner

*Primary Examiner*—Jill Warden
*Assistant Examiner*—Neil Turk
(74) *Attorney, Agent, or Firm*—Cardinal Law Group (57) ABSTRACT

Samples of materials used in industrial processes are analyzed to determine the concentration of certain materials of interest. The quantitative analysis of samples for these materials is provided without the need for manual methods such as titration. Indicators such as fluorescent dyes for which the intensity of fluorescence is indicative of the concentration of a material of interest are used. The dyes are made to fluoresce by means of a light source, and a photomultiplier or other detector capable of measuring light intensity detects the resulting fluorescence. The intensity of fluorescence in the sample is compared to the intensities of fluorescence produced by samples with known concentrations of the material of interest to determine the concentration of the material of interest of the sample.

7 Claims, 5 Drawing Sheets

AUTOMATED SAMPLE ANALYSIS

RELATED APPLICATIONS

This application is based on U.S. Provisional Application Ser. No. 60/469,431, filed May 9, 2003.

BACKGROUND OF THE INVENTION

1. Field of the Invention

The present invention relates to the field of specimen analysis, and methods and apparatus therefor. More particularly, the invention relates to the field of specimen analysis for monitoring and controlling industrial, agricultural, mineral exploration and similar processes and operations.

2. Description of the Related Art

The need to monitor or control an operation or process arises in many industrial operations. Such industrial operations include the manufacture of goods, and the exploration for and production of minerals. Frequently, the data required to monitor or control an operation or process is generated by a chemical analysis that determines the presence or quantity of certain materials. These materials may be used in the process, or they may be undesirable contaminants. For example, some fluids used in manufacturing environments are cycled through an entire factory and used in multiple locations therein. The effectiveness of the fluids may rely on the presence of multiple additives therein, which are exhausted over the course of use, and must be replenished. The determination of when to replenish the additives, and in what amount, is often left up to a technician who takes a sample of the fluid and analyzes it using manual, visual titration techniques to determine the quantity of different additive materials present. Each sample is analyzed for the presence or absence of one or more specific materials desired to be present in the fluid, and the quantities thereof in the sample dictate whether to add additives to the fluid, and if so, the amounts of additives to add to the fluid to restore it to its intended composition. Errors inherent in this analysis, which relies upon the judgment of the technician to determine the quantities of additives in the samples, can result in inadequate or improper addition of the additives, resulting in decreased performance of the fluid for its intended purpose. Likewise, some fluids used in manufacturing processes may become contaminated with undesirable materials. For example, it may be illegal to discharge fluids from industrial, chemical, mineral exploration and other sites when those fluids contain certain levels of hazardous materials. Therefore, the discharged fluid must be analyzed for the presence and quantity of those hazardous materials. In many industrial settings, this analysis is again made manually, typically through visual titration techniques, and errors in the analysis can result in the unwanted discharge of hazardous materials, or the perceived inability to discharge fluid streams that are properly dischargeable.

Microfluidic devices, which are widely used in the analysis of biological materials, have not been widely used to analyze samples from industrial processes. Microfluidic devices are devices comprising fluidic elements that have at least one fabricated dimension in the range of from about 0.1 µm to about 500 µm. Fluidic elements are structures through which fluid can flow, such as passages, channels, chambers or conduits. So the fluidic elements in microfluidic devices typically have at least one internal cross-sectional dimension (e.g., depth, width, length, diameter, etc.) between about 0.1 µm and about 500 µm. Microfluidic devices have found a wide range of applications in the analysis of biological materials. For example, microfluidic devices have been employed to perform various analyses on nucleic acids such as RNA and DNA, to screen biological samples for therapeutic properties, and to determine the concentration of certain ions within a cell. The use of microfluidic devices has been almost exclusively limited to the analysis of biological materials largely because the concentration of the components of interest in biological samples, and the pH of those samples, are within relatively narrow and predictable ranges. Having the concentration of components of interest within a narrow and predictable range allows the concentration of reagents used in an analysis to be predetermined before the analysis is performed. For example, many fluorescent dyes used to label components of interest in an analysis are only effective over a certain concentration range of the material the dyes detect. In general, the dyes are only effective with trace concentrations of the materials of interest. More specifically, a fluorescent dye can be used to quantify the concentration of the material detected by the dye when the intensity of fluorescence of the dye predictably varies with the concentration of the labeled material. However, fluorescent dyes only have a limited dynamic range, meaning that the level of fluorescence is indicative of the concentration of the material over a narrow range of concentration. Similarly, many of those fluorescent dyes are only effective within a certain range of pH. Thus it would be very difficult to employ a fluorescent dye to analyze a sample in which the pH and the concentration of the material of interest is completely unknown, as is typically the case for samples of fluids from industrial operations. Nevertheless, it would be desirable to employ microfluidic devices to analyze those fluids because analyses carried out in microfluidic devices are rapid, precise, and easily automated. Another factor limiting the application of microfluidic devices to the analysis of industrial fluids is that the level of fluorescence generated by a sample may vary between individual microfluidic devices. Thus an individual device would have to be calibrated before the device could produce accurate data.

Thus, there is a need in the art for methods and apparatuses for analyzing fluids used in industrial processes that are not reliant on human judgment and skill for the analytical result, and that have greater reproducibility. This need could be satisfied through the application of microfluidic devices.

SUMMARY OF THE INVENTION

The present invention provides methods and apparatuses for the analysis of samples of fluids from industrial operations, in which the analysis provides both quantitative and qualitative results without the need for operator interpretation. In one aspect, a microfluidic device is provided that has a multiplicity of wells therein into which quantities of a control sample, the sample to be analyzed, indicators, buffers and any other needed analytical consumables are provided. The wells are in fluid communication with specific channels within the device such that the sample received therein is mixed, in the channels, with the indicator or other analytical substance, and the resulting mixture is analyzed for a result indicative of the presence and quantity of selected constituents of the sample.

In one aspect, the indicators include fluorescing compounds or materials, which when exposed to specific materials present in the sample within a desired range of concentration or quantity, fluoresce and thereby provide a signal indicative of the presence of a specific material in the sample being analyzed, as well as of the quantity of the material. Preferably the microfluidic device is interfaced with a standalone instrument, i.e., an instrument which includes all control and reporting peripherals and software therein, such that once the sample is prepared for analysis, the standalone instrument directs any additional diluting and the mixing of samples, indicators and buffers necessary to enable analysis without further operator or technician intervention. In one aspect, the instrument and microfluidic device, in combination can be self-calibrating by comparing sample data to one or more reference samples having known concentrations of the constituent of interest. In an additional aspect, the small dimensions of the fluidic elements in the microfluidic device enable small amounts of sample, indicator and other reagents to be utilized to determine the properties of interest of the sample. In yet another aspect, the analysis determines the concentration of ions of inorganic substances in a sample.

In an additional aspect, the samples for analysis are provided from industrial, manufacturing, refining, mineral exploration, and related processes and operations, and the constituents thereof being analyzed are indicative of the status of a process or of the condition of a fluid. In response to the results of the analysis, the process or operation may be modified, or the concentration of constituents of the fluid changed, where the results of the analysis indicate the necessity to do so.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION OF THE INVENTION

The present invention provides methods and apparatus for the analysis, such as the chemical analysis, of samples of materials for selected properties thereof, and in particular, enables relatively rapid and accurate quantitative analysis of chemicals in non-biological samples, which quantities are indicative of the relative status or correctness of an industrial process, or condition of the material from which the sample was taken. The methods and apparatus are applicable to the replacement of traditional laboratory analysis techniques, and have the particular advantage of being compact in size, relatively easy to use, and not subject to operator interpretation to provide the resulting determination of the quantity of a substance or constituent present in a sample. In one aspect, the analysis relies on the reaction of dyes that fluoresce when exposed to light within a specific wavelength range with a material of interest that may be present in a sample. By analysis of the magnitude of the resulting fluorescence, the quantity of the material of interest in the sample is calculable, and is preferably provided by logic elements provided in an analysis apparatus or instrument. In a further aspect, the analysis of a sample may be provided in conjunction with the analysis of a known baseline or control sample, and the fluorescence of that sample used to calibrate the analysis for every sample analyzed, and thereby eliminate any issues of process or instrument drift of the instrument, as well as variation between microfluidic devices used for the analysis. The analysis is preferably undertaken on a microfluidic device having fluid circuitry thereon, such that the mixing and detection of the sample, once on the device, is fully automated and thus not susceptible to operator error.

Figure 1:
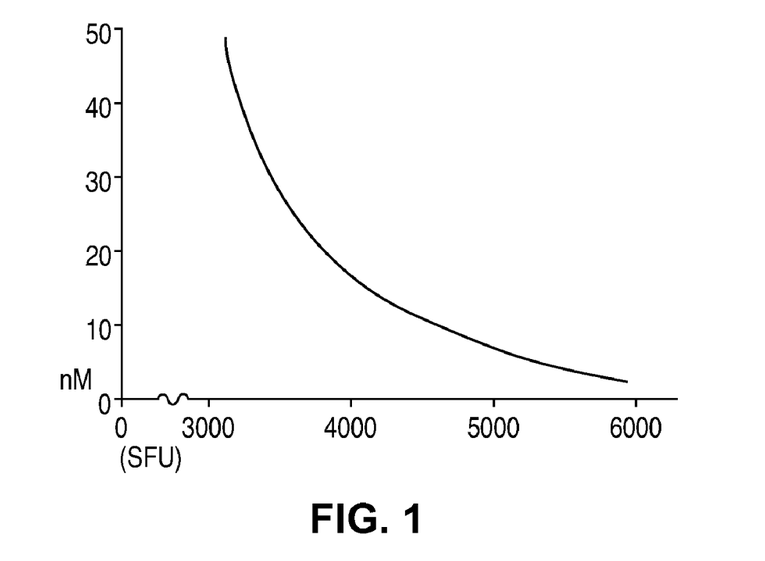
FIG. 1 is the response curve of an exemplary fluorescent dye.

The role of the indicators in embodiments of the invention is to provide a detectable indication of the presence of the material of interest. In various embodiments, such a detectable indication could be provided by a reaction between the indicator and the material of interest that changes a detectable signal produced by the indicator. For example, the indicator could be a fluorescent dye that fluoresces when it reacts with the material of interest, or the indicator could be a fluorescent dye whose fluorescence is quenched by the material of interest. In other embodiments, the reaction between the indicator and the material of interest could produce a chemiluminescent product, quench the chemiluminescence of the indicator, or change the color of the indicator. In embodiments employing a fluorescent dye, the fluorescent dye can provide quantitative results when the amount of dye that fluoresces correlates with the concentration of the material of interest. Such a correlation can occur, for example, if the dye selectively binds to the material of interest, or if the material of interest undergoes a selective reaction with the dye that causes the dye to fluoresce. When using such a fluorescent dye, the quantity of the material of interest in a sample would be indicated by the intensity of the fluorescence produced by the dye when a laser or other light source of appropriate wavelength illuminates the dye. An example of a fluorescent dye compatible with embodiments of the invention is lucigenin, available from Molecular Probes, Inc. of Eugene, Oreg., which fluoresces at a wavelength of approximately 505 nm when excited by shorter wavelength light. The fluorescence of lucigenin is quenched in the presence of chloride ions, so a reduction in lucigenin fluorescence corresponds to an increase in chloride ion concentration. In addition to lucigenin, Molecular Probes markets compounds that could serve as indicators for calcium ions, sodium ions, potassium ions, iodide ions, cyanide, sulfides, sulfates, sulfites, nitrites, phosphates, pyrophosphates, selenium, and cesium. For most indicators, to obtain a quantitative measurement of the concentration of the material of interest from the level of detectable signal produced by the indicator, the concentration of the material of interest must be within the dynamic range of the indicator. In other words, most indicators have limited dynamic ranges such that above a certain concentration of the material of interest a further increase in concentration results in no discernable change in detectable signal. In addition, for many indicators the level of detectable signal does not vary with the concentration of the material of interest in a linear fashion. For example, as shown in FIG. 1, the level of fluorescence (plotted along the x-axis) from lucigenin is not a linear function of chloride concentration. Embodiments of the present invention can compensate for such non-linear behavior by comparing the fluorescence produced by a sample to the fluorescence produced by reference samples with different known concentrations. The range of the known concentrations is selected so that it spans a likely concentration of the material of interest in the sample, and so that it is within the dynamic range of the dye. In FIG. 1, the level of fluorescence from the lucigenin monotonically decreases as the chloride concentration increases, so the chloride concentration range is within the dynamic range of lucigenin. In some embodiments the microfluidic device performing the analysis is configured so that it is capable of diluting a single reference sample to multiple dilution levels. This provides the capability to obtain multiple reference samples from a single source. Similarly, in some embodiments the microfluidic device performing the analysis is configured so that it is capable of diluting the sample being analyzed. The ability to dilute the sample being analyzed makes it possible to bring a sample containing too high a concentration of the material of interest to be diluted so that the concentration of the material of interest is within the dynamic range of the dye. In other embodiments, dilution of the sample may take place within the instrument before the instrument places the sample in the microfluidic device. In still other embodiments, the sample may be diluted before it is placed into the instrument.

I. A Microfluidic Device Interfaced with a Multiport Fluid Control System

Figure 2:
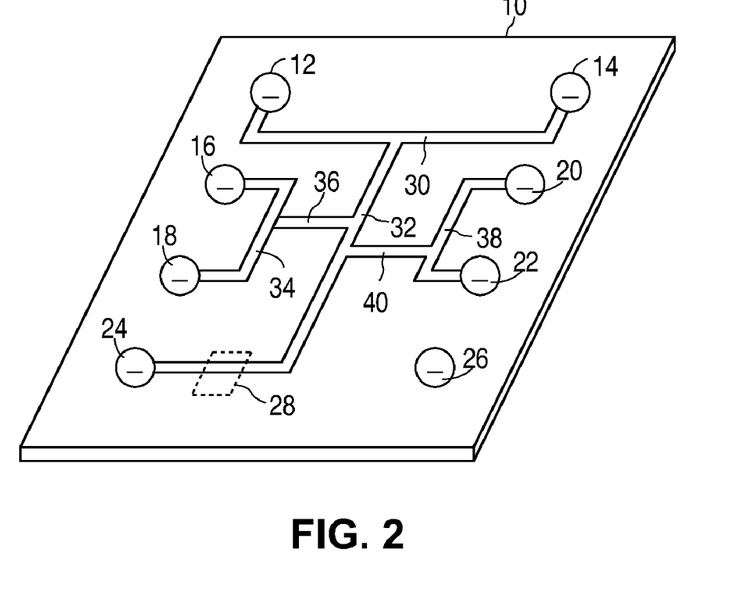
FIG. 2 is a perspective view of a microfluidic device useful in the practice of the present invention.

FIG. 2 shows an example of a microfluidic device 10 useful in the practice of embodiments of the present invention. As will be described in more detail later, a microfluidic device such as device 10 is typically used in conjunction with an instrument like those shown in FIGS. 6 and 8. The microfluidic device 10 includes a plurality of reservoirs that may be used to introduce fluids into, or to collect waste fluids from, channels in the microfluidic device. The reservoirs in FIG. 2 include a reference sample well 12 containing a reference sample having a known concentration of the material of interest; a first buffer well 14 containing a supply of buffer; a sample well 16 containing a sample having an unknown concentration of the material of interest; a second buffer well 18; first and second indicator wells 20, 22 each containing a solution comprising an indicator, and a waste well 24 in which effluent is stored. An additional well 26 may also be provided, but it is unnecessary for this embodiment of the invention.

The various reservoirs or wells are fluidly connected through channels 30-40 within the device 10. Reference sample well 12 and first buffer well 14 are connected through control sample channel 30. Sample well 16 and second buffer well 18 are likewise connected through sample channel 34. The control sample channel 30 is directly connected to main channel 32, while sample channel 34 is connected to main channel 32 through sample feed channel 36. During operation of device 10, samples from sample wells 12 and 16 are transported through the main channel 32 toward waste well 24. The intersection of sample feeder channel 36 with main channel 32 is located intermediate of waste well 24 and the intersection of control sample channel 30 with main channel 32. Indicator wells 20 and 22 are connected to main channel 32 through indicator channel 38 and indicator feed channel 40. The indicator feed channel 40 intersects main channel 32 intermediate of waste well 24 and the intersection of sample feed channel 36 with main channel 32, which means that the one or more indicators are introduced into the main channel 32 downstream of where samples are introduced into the main channel. After samples are mixed with one or more indicators, the resulting mixture flows through the main channel past the detection region 28 into the waste well 24.

Within sample channels 30 and 34, samples from the sample wells 12 and 16 can be diluted with buffer from buffer wells 14 and 18 (respectively) before the sample flows into main channel 32. The sample, which may or may not have been diluted with buffer, is then mixed with one or more indicators from indicator wells 20, 22. In embodiments where one indicator is used, the indicator flows out of one of indicator wells 20, 22. The presence of two indicator wells 20, 22 would allow device 10 to assay samples for more than one material of interest since two different indicators are available. In most cases, the assays using the two different indicators would take place separately. The two assays could be carried out simultaneously if each indicator does not interfere with the other indicator's reaction with its material of interest, if the indicators can be separately detected, and when quantitative analysis for each material of interest is desired if the dynamic ranges of the indicators overlap. Once mixed with the one or more indicators, the sample would flow through the main channel 32 into a detection region 28 in which the signal or signals emanating from the one or more indicators can be detected by a detector (not shown).

The microfluidic device 10 is specifically capable of providing different levels of dilution of the samples from the sample wells 12 and 16. By providing different dilutions of the reference sample in reference sample well 12, the device 10 can be used to generate a response curve such as that shown in FIG. 1. Such a response curve would provide the correlation between detectable signal (e.g. fluorescence) and concentration of the material of interest that is necessary to determine the concentration of the material of interest in a sample of unknown concentration. By providing different dilutions of the sample of unknown concentration in sample well 16, the device 10 could be used to dilute the sample of unknown concentration sufficiently so that the concentration of the material of interest in the diluted sample is within the dynamic range of the indicator.

The dilution of samples, mixing of diluted or undiluted samples with one or more indicators, and movement of the sample/indicator mixture through the detection region 28 is accomplished by controlling the flow of fluids through channels 30-40 in device 10. The flow of fluids through the individual channels 30-40 is controlled by applying separately controllable driving forces to each of the reservoirs 12-24. A fluid control system capable of applying separately controllable driving forces to each reservoir in a microfluidic device can be referred to as a multiport control system. Multiport control systems can employ a variety driving forces. For example, a multiport control system can employ electrokinetic forces to initiate fluid flow through channels 30-40 by immersing electrodes in each of reservoirs 12-24, and by applying a separately controlled voltage to each electrode. Examples of multiport control systems that employ electrokinetic forces are described in U.S. Pat. Nos. 5,965,001 and 5,858,195. For many samples from industrial processes, however, the application of electric fields to the sample may adversely affect the results of an analysis. For example, a sample containing a variety of charged species may become distorted in an electric field because the electric field would tend to electrophoretically separate the various charged species. Accordingly, it is often preferable to employ a pressure-based fluid control system in embodiments of the invention. A pressure-based multiport control system for the embodiment of FIG. 2 would separately control the relative pressure applied to each reservoir 12-24 in fluid communication with the channels 30-40 of the device. An example of such a pressure-based control system is described in PCT Publication Number WO 01/63270. A pressure-based multiport control system for the device 10 in FIG. 2 could pneumatically apply separately controlled pressures to each of reservoirs 12, 14, 16, 18, 20, 22, and 24. This could be accomplished by interfacing each of those reservoirs to a pressure transmission lumen (not shown) connected to a pressure source (not shown). Pressure is then transmitted from the pressure source to the surfaces of the fluids in the reservoirs through a fluid (typically air) in the lumens. For the microfluidic device shown in FIG. 2, a pressure source that could vary the pressures applied to the reservoirs by plus or minus 5 psi from a baseline level would be adequate. By selectively applying individual relative pressures to the reservoirs 12 to 24, the flow rates through each individual channel 30-40 can be controlled. In many embodiments, applying pressures greater than a baseline pressure to a first set of reservoirs will cause fluid to flow out of those reservoirs toward a second set of reservoirs to which pressures less than the baseline are applied. In those embodiments, applying the baseline pressure to a third set reservoirs will prevent any flow in or out of that third set of reservoirs. Thus, for example, in the embodiment of FIG. 2 the combination of a baseline pressure applied to each of sample well 16, second buffer well 18 and second indicator well 22; a higher-than-baseline pressure applied to reference sample well 12, first buffer well 14 and first indicator well 20; and a lower-than-baseline pressure applied to waste well 24 would cause a mixture of reference sample from reference sample well 12 and buffer from first buffer well 14 to flow into main channel 32 and mix with indicator flowing from first indicator well 20. The mixture of diluted sample and indicator would then flow past detection region 28 into waste well 24. The relative quantity of reference sample from reservoir 12 and buffer from reservoir 14 flowing into main channel 32 can be varied by varying the relative magnitudes of the higher-than-baseline pressures applied to reference sample well 12 and first buffer well 14. Thus it is possible to control the dilution level of the reference sample, providing the ability to create a variety of samples with known concentrations of the material of interest.

In one embodiment of the invention, the device 10 in FIG. 2 can carry out a quantitative analysis of a sample containing an unknown concentration of a material of interest. The first step in the quantitative analysis would be to measure the level of detectable signal generated by a plurality of samples with known concentrations of the material of interest. As previously discussed, a plurality of samples with known concentrations of the material of interest can be generated by diluting reference sample from reference sample well 12 with buffer from first buffer well 14. Varying the relative pressures applied to wells 12 and 14 controls the amount of dilution of the reference sample. The concentrations of the plurality of samples with known concentrations preferably lie within the dynamic range of the indicator used to generate the detectable signal. The detectable signals generated by the plurality of samples of known concentration are measured as those samples pass through the detection zone 28. The detectable signals produced by the samples of known concentration provide the means for converting detectable signals produced by samples of unknown concentration into concentration measurements. In general, samples of unknown concentrated are diluted until the concentration of the material of interest is within the dynamic range of the indicator. In device 10, a sample with an unknown concentration of the material of interest in sample well 16 is introduced intro the main channel 32 by applying a higher-than-baseline pressure to sample well 16, second buffer well 18, and second indicator well 22, applying a lower-than-baseline pressure to waste well 24; and applying the baseline pressure to reference sample well 12, first buffer well 14, and first indicator well 20. By varying the relative magnitudes of the higher-than-baseline pressures applied to wells 16 and 18, the detectable signals from various dilutions of the sample of unknown concentration can be measured. For essentially all samples of fluids from industrial processes, the concentration of the material of interest will exceed the maximum concentration in the dynamic range of the indicator. Accordingly, the analysis of such a sample will typically comprise successively diluting the sample with increasing amounts of buffer from second buffer well 18 until changes in dilution of the sample produce variations in the detectable signal that correspond to the variations of detectable signal with concentration in the dynamic range of the indicator. When the sample with an unknown concentration of the material of interest is sufficiently diluted so that the concentration of the material of interest in the diluted sample is within the dynamic range of the indicator, the level of detectable signal from that diluted sample will correlate with the concentration of the diluted sample. The concentration of the original sample with an unknown concentration can be calculated from the measured concentration of the diluted sample and the degree to which the original sample was diluted.

The correlation between concentration of the material of interest and detectable signal within the dynamic range of the indicator is determined by measuring the detectable signal produced by different dilutions of the reference sample. For example, the curve in FIG. 1 represents the correlation of chloride ion concentration with the detectable fluorescence produced by the fluorescent dye lucigenin. The device in FIG. 2 could produce the correlation in FIG. 1 by diluting a 100 mM solution of NaCl in 10 mM Tris buffer in reference sample well 12 with various amounts of a 10 mM Tris buffer solution in well 14. Using the correlation in FIG. 1, the concentration of a sample of unknown concentration of chloride can be found by diluting the sample until the fluorescence produced by a mixture of the diluted sample and lucigenin produces a fluorescence level of between 3000 and 6000 SFU, locating the concentration of chloride corresponding to the fluorescence level of the diluted sample, and finally calculating the concentration of chloride in the original sample by adjusting the concentration determined by the correlation to compensate for the dilution of the sample.

In the device 10 shown in FIG. 2, the sample in sample well 16 can be analyzed for a second material of interest if an indicator for that second material of interest is stored in second indicator well 22, and if the above described analysis is carried out using the indicator in the second indicator well 22 in place of the indicator in the first indicator well 20. In some embodiments, the sample in sample well 16 could be simultaneously assayed for two materials of interest if each of the different indicators in indicator wells 20,22 does not interfere with the other indicator's reaction with its associated material of interest, if the indicators can be separately detected. If a simultaneous quantitative analysis for two materials of interest is desired, then the dynamic ranges of the two indicators must overlap.

When interfaced with an appropriate instrument, microfluidic device 10 can be used to quantitatively determine the concentration of one or more materials of interest in a sample of fluid from an industrial process. This quantitative determination is completely automated, rapid, and precise. The use of a multiport control system provides a great deal of flexibility that enables microfluidic device 10 to be employed in a variety of different analyses. Unfortunately, multiport control systems are typically complex mechanical or electrical devices. This complexity increases cost and reduces reliability. Accordingly, in some embodiments it may be desirable to employ a microfluidic device that does not require a multiport control system.

II. Microfluidic Devices for Simplified Fluid Control Systems

Figure 4:
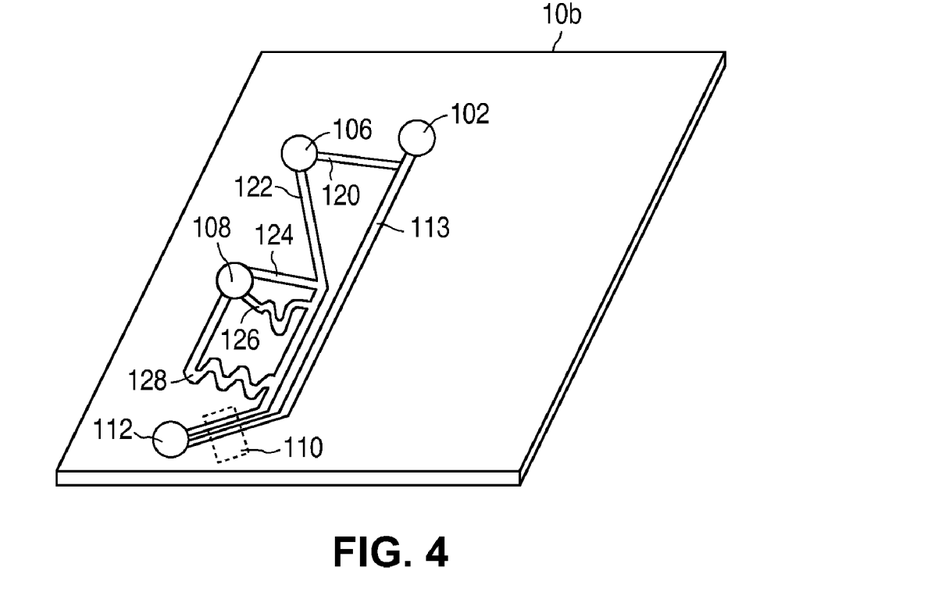
FIG. 4 is a perspective view of an additional microfluidic device for practicing the present invention.
Figure 5:
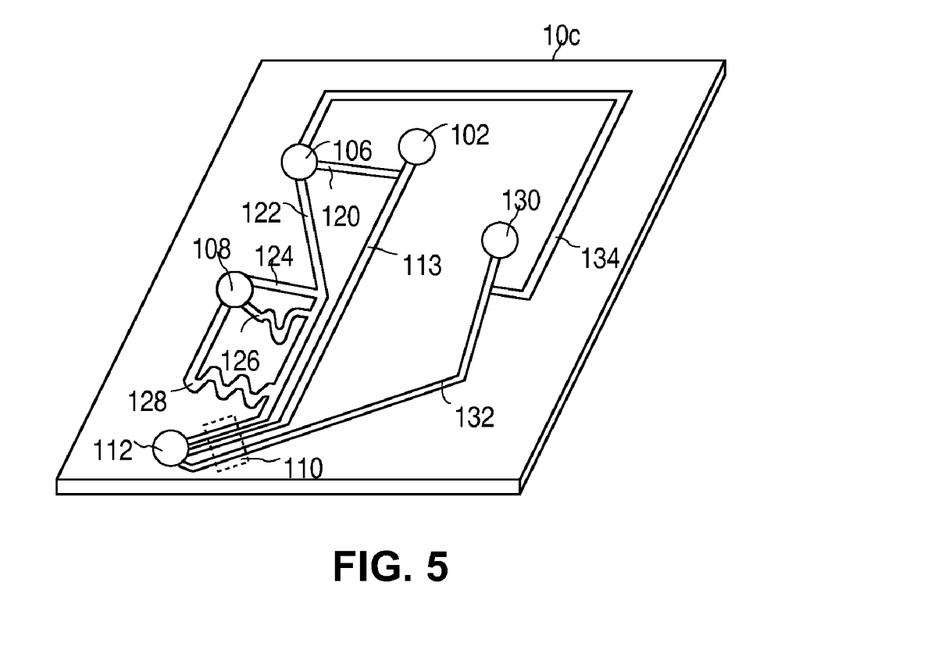
FIG. 5 is a perspective view of an additional microfluidic device for practicing the present invention.

In some embodiments of the invention, fluid flow through the channels of the microfluidic device in which analyses are performed is initiated by applying a single vacuum source to one well on the microfluidic device. When the single driving force is applied to a fluidly connected set of channels, the flow rate through each channel is determined by that channel's flow resistance. A channel's flow resistance is primarily a function of the geometry of the channel. For example, the flow resistance of a channel decreases as the cross-sectional area of the channel increases, decreases as the channel depth increases, and increases as the channel length increases. The relationships between channel geometry and flow resistance are well known to those in the art. Thus the flow rates through individual channels in an interconnected network of channels in a microfluidic device can be programmed for a particular vacuum level by appropriately configuring the geometry of channels in the microfluidic device. A microfluidic device in which flow rates are controlled in this manner is described in US Published Application No. 2002/0019059. The desirable decrease in complexity provided by a single vacuum source control system is accompanied by an undesirable decrease in flexibility. Since the flow rates through the channels of microfluidic device interfaced with a single vacuum source are determined by the geometry of those channels, the device is essentially hardwired for a single flow pattern. In contrast, the flow pattern in a microfluidic device interfaced to a multiport control system can be changed by changing the driving forces applied to the various reservoirs. As will be discussed in more detail below, the microfluidic devices in FIGS. 3, 4, and 5 are compatible with single vacuum source control systems.

A. Multiple Sample and Control Sample Dilutions

Figure 3:
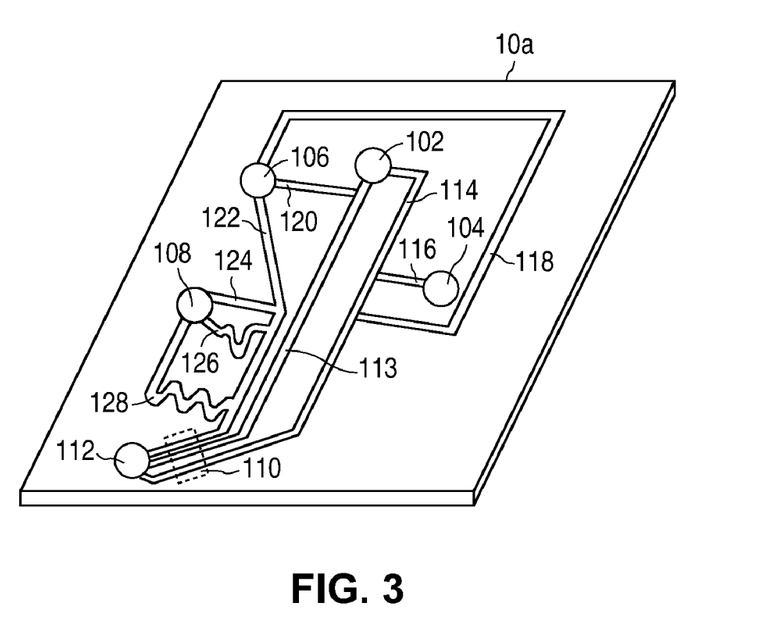
FIG. 3 is a perspective view of an additional microfluidic device for practicing the present invention.

FIG. 3 shows a microfluidic device 10a useful for practicing embodiments of the present invention involving single vacuum source control systems. Device 10a comprises a sample well 102 containing a sample with an unknown concentration of the material of interest, a reference sample well 108 containing a reference sample with a known concentration of the material of interest, a buffer well 104 containing a buffer for diluting the sample from well 102, an indicator well 106 containing an solution comprising an indicator that produces a detectable signal that varies with the concentration of the material of interest when that concentration is within the dynamic range of the indicator.

When a vacuum is applied to waste well 112, and the remaining wells 102, 104, 106, 108 are left open to the atmosphere, the resulting pressure driving force will initiate a flow from those wells through channels 113, 114, 118, 120, 122, 124, 126, 128 toward waste well 112. The resulting flow pattern through the device 10a can be understood by tracing the flow from the sample reservoirs 102, 108. When a vacuum is applied to waste well 112, the reference sample in reference sample well 108 will begin to flow through channels 124, 126, and 128 into channel 122. Channel 122 extends from indicator well 106, through detection region 110, to waste well 112. The flow resistance of the portion of channel 122 extending from indicator well 106 to the intersection with channel 124 is made low enough so that indicator flowing from indicator well 106 arrives at the intersection of channel 122 with channel 124 at the same time or before reference sample arrives at that intersection. In this way, any reference sample arriving in channel 122 will be mixed with indicator from indicator well 106. Of the three channels 124, 126, 128 emanating from reference sample well 108, channel 124 has the lowest flow resistance (e.g., because it may be shorter), channel 126 has a higher flow resistance, and channel 128 has the highest flow resistance. Thus the amount of reference sample flowing through channel 122 will at first consist of only the reference sample flowing through channel 124. When sufficient time has elapsed so that reference sample from reference sample well 108 has passed through the longer channel 126, the amount of reference sample flowing through channel 122 will consist of the increased amount of reference sample flowing through both channels 124 and 126. Finally, when sufficient time has elapsed so that reference sample from reference sample well 108 has had enough time to pass through the longest channel 128, the amount of reference sample flowing through channel 122 will consist of the further increased amount of reference sample flowing through the three channels 124, 126, 128. The three different amounts of reference sample, representing the cumulative flow from one, two or three channels, result in three different known concentrations of the material of interest flowing past detection region 110. The three concentrations are known because the concentration of the material of interest in the reference sample is known, the flow rates of each of the three channels 124,126, 128 leading from reference sample well 108 can be determined from the channel geometries, the flow rate of indicator solution through channel 122 can be determined from the channel geometry, and the composition of the indicator solution is known. The three known concentrations of the material of interest preferably lie within the dynamic range of the indicator so that a correlation between detected signal and concentration, such as that shown in FIG. 1, can be generated.

When a vacuum is applied to waste well 112, a sample containing an unknown concentration of the material of interest flows from sample well 102 through channels 113 and 114. The portion of the sample flowing through channel 113 is mixed with indicator flowing through channel 120, and the resulting mixture flows past detection region 110 into waste well 112. The portion of the sample flowing through channel 114 is diluted with buffer flowing from buffer well 104 through channel 116. This diluted sample is then mixed with indicator flowing from channel 118, and the resulting mixture flows past detection region 110 into waste well 112. The level of dilution is determined by the relative flow rates through channels 114 and 116, which are function of the geometry of those channels. Since the concentration of the material of interest in the sample in sample well 102 is unknown, providing the two different dilutions of the sample in channels 113 and 114 increases the chance that the concentration in one of the two dilutions will lie within the dynamic range of the indicator. In general, the concentrations of materials of interest in samples from industrial processes far exceed the dynamic range of the indicators used to detect those materials. Accordingly, the sample taken from an industrial process is usually diluted before it is placed in sample well 102. The original sample from an industrial process may have to be manually diluted to a number of different dilution levels before a dilution producing a concentration of the material of interest within the dynamic range of the indicator is found. By providing an addition level of dilution on the device 10a, the number of dilution levels that have to be manually produced is reduced. Although device 10*a* produces only two dilution levels, other embodiments of the invention could provide three or more dilution levels.

One advantageous feature of the embodiment in FIG. 3 is that the correlation between concentration of the material of interest and the level of detectable signal produced by the indicator is generated on the same microfluidic device 10*a* on which samples of unknown concentration are measured. A model may be generated representative of the signal from each of the dilutions of the control and the relative ratio of the control and the indicator. The signal from a sample of unknown concentration is then compared within the model, providing a determination of the concentration of the material of interest present in the sample of unknown concentration.

Generating the concentration/signal correlation on the same device on which measurements are taken helps eliminate measurement inaccuracies that could occur when sample measurements are compared to correlations produced by other methods or in different microfluidic devices. These inaccuracies could come from a variety of sources including instrument drift and variations between different microfluidic devices. Thus, the microfluidic device 10*a* can be thought of as having an inherent calibration capability.

There are a number of practical considerations that must be taken into account when using microfluidic devices that interface with single vacuum source control systems instead of multiport control systems. For example, microfluidic devices that interface with a single vacuum source, such as the microfluidic devices 10*a*, 10*b*, and 10*c* in FIGS. 3, 4, and 5, must be primed before they can be used to carry out an analysis. The priming step is carried out before the wells 102,104,106,108 are filled with the samples, buffer, and indicator solution required to perform an analysis. Typically, the priming step is carried out during manufacture of a microfluidic device by providing a nozzle or spout to the waste well 112 and introducing buffer fluid therein until the buffer is flowing out of every other well of the device. By priming the device 10*a* during manufacture, the instrument that carries out analyses using the microfluidic device does not have to have the ability to prime the device. Another consideration when using a microfluidic device such as those in FIGS. 3, 4, and 5 is that signals from each of the multiple channels passing through the detection region must be individually detected. For example, in the microfluidic device 10*a* of FIG. 3, signals from each of channels 122, 113, and 114 must be individually detected. An instrument interfaced with the microfluidic device can accomplish this, for example, with a moveable detector, or with multiple detectors. Embodiments of instruments with moveable detectors are described herein.

B. Single Sample Concentration and Multiple Samples

FIG. 4 shows yet another example of a microfluidic device 10*b* compatible with a single vacuum source control system. Microfluidic device 10*b* is a simplified version of the device 10*a* in FIG. 3. This simplified version can be used when the concentration of the material of interest in a sample is within the dynamic range of the indicator. When this is the case, there is no need to further dilute the sample. Therefore, the features of the device 10*a* that enable dilution, which include buffer well 104, and channels 114, 116, and 118, can be eliminated. Apart from the deletion of those features, the design and operation of the simplified device 10*b* in FIG. 4 is essentially identical to the previously described design and operation of device 10*a* of FIG. 3.

FIG. 5 shows another microfluidic device 10*c* in accordance with embodiments of the invention. The device 10*c* is able to analyze two samples with unknown concentrations of the same material of interest. The ability to analyze two samples of unknown concentration is provided by adding to the embodiment of FIG. 4 a sample well 130 to contain the second sample with an unknown concentration of the material of interest, a channel 132 that fluidly connects the sample well 130 to the waste well 112, and a channel 134 that fluidly connects indicator well 106 to channel 132. Thus, when a vacuum is applied to waste well 112, a mixture comprising the second sample fluid disposed in second sample well 130 and indicator solution supplied from indicator well 106 will be drawn through detection region 110 in second sample channel 132. The second sample could be a sample from a different industrial process than the first sample, from the same industrial process as the first sample but taken at a different location or time, or a diluted version of the sample located in sample well 102. Thus, device 10*c* in FIG. 5 can analyze multiple samples for the concentration of a single material of interest therein.

III. An Instrument that Interfaces with the Microfluidic Devices

Figure 6:
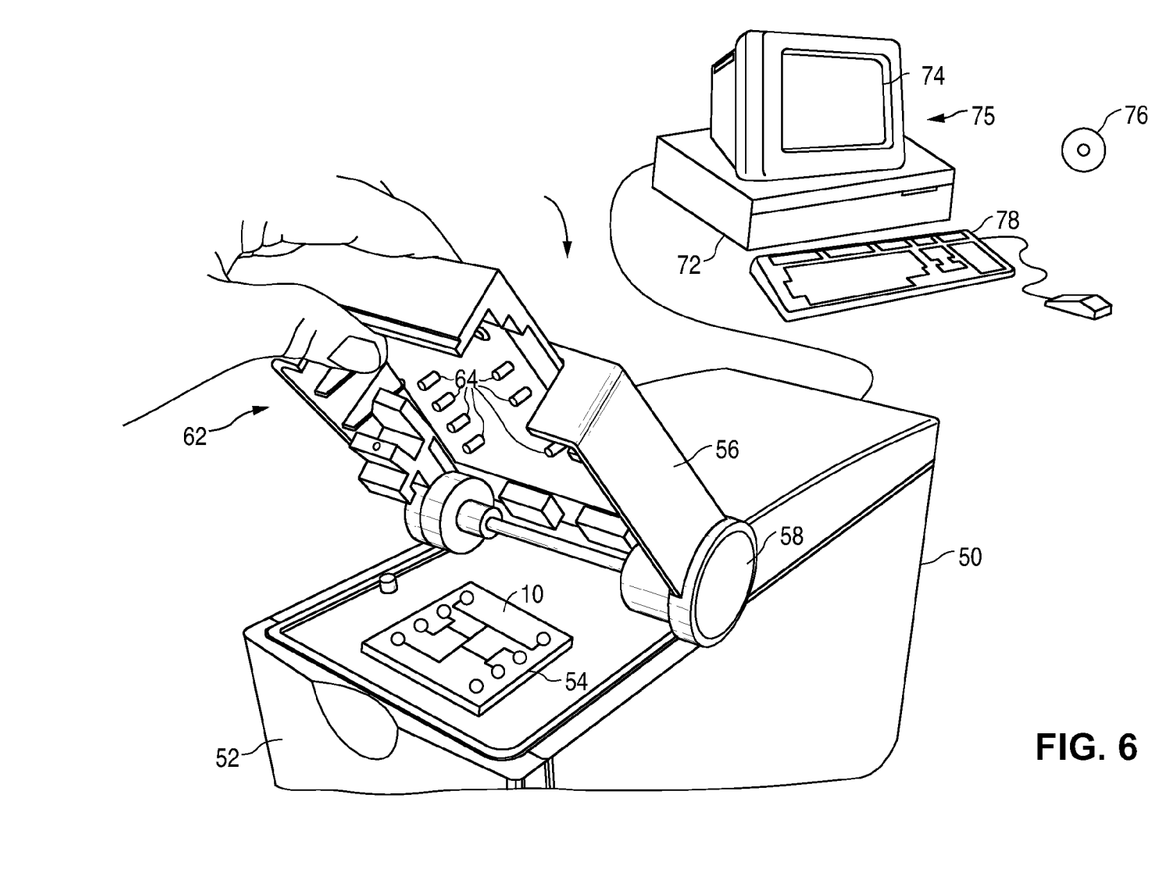
FIG. 6 is a partial perspective view of an instrument compatible with the device shown in FIG. 2.

To enable the passage of fluids through the channels of the microfluidic devices 10, 10*a*, 10*b* and 10*c*, as well as to enable the detection of the detectable signal produced by the indicator mixed with samples of unknown concentration and reference samples, there is provided an instrument 50 as shown generally in FIG. 6. Instrument 50 generally includes a base 52, upon which a microfluidic device such as device 10 in FIG. 2 is located in an appropriate carrier 54 and positioned for evaluation. A cover plate 56, is arcuately actuable about hinge 58 between a closed position wherein the cover plate 56 is disposed substantially parallel to the surface of device 10 and a loading position 62 as shown in FIG. 6 wherein the cover plate 56 is swung upwardly from the base 52 to allow removal of a microfluidic device 10 in the instrument or the placement of a microfluidic device 10 therein. To align microfluidic device 10 with the structures of the instrument 50, device 10 and or the carrier 54 include an alignment tab, alignment notch, or the like (not shown), which mates with an alignment tab (not shown) in the base 52. This tab or notch may also, in conjunction with one or more switches or indicators on the instrument, provide information about the type of sample and thus the type of indicators present in the device 10. As a result, the detection region of the device 10 is properly aligned with a window 60 (see FIG. 7) in base 52 over which the device 10 is positioned in the instrument 50. Within cover plate 56 are located a plurality of lumens 64 in fluid communication with a pressure source capable of applying relative pressures to the wells of the device 10 that are in a range of about plus or minus 5 psi relative to a baseline pressure. By varying the pressures applied to the wells of device 10, different mixtures of samples, buffer, and indicator can be generated within the channels of the device 10.

Referring again to FIG. 6, instrument 50 also includes a controller section 72, within which are provided a system controller 75 responsive to the opening and closing of the cover plate 56, and also responsive to user input to the instrument through a GUI 74 or a keyboard 78. Preferably, the controller section 72 is preprogrammed with analysis scripts, and the user selects a desired script for analysis of a specific sample on specific microfluidic device. The scripts may be preprogrammed into the controller, may be added to the controller through an interface such as a CD ROM 76 locatable in a CD drive, or an internet connection, or may be provided by programming directly into the controller by a technician or programmer, etc. Although the controller section 72 is shown as a separate computer, keyboard and mouse connected to the instrument, the controller may also be integrally provided within the instrument 50, and the only outputs of the instrument may be provided on a readable screen (not shown) physically located on the instrument and displaying relevant information about the sample and the status of the instrument. For an analysis using a microfluidic device 10, this controller is used to both determine the appropriate driving forces to apply to the wells, based upon an input to the controller of the analysis and the configuration of the microfluidic device (which is preferably preprogrammed and user selectable), as well as to cause application of the driving forces as needed to provide the movement of fluid within the device 10.

Figure 7:
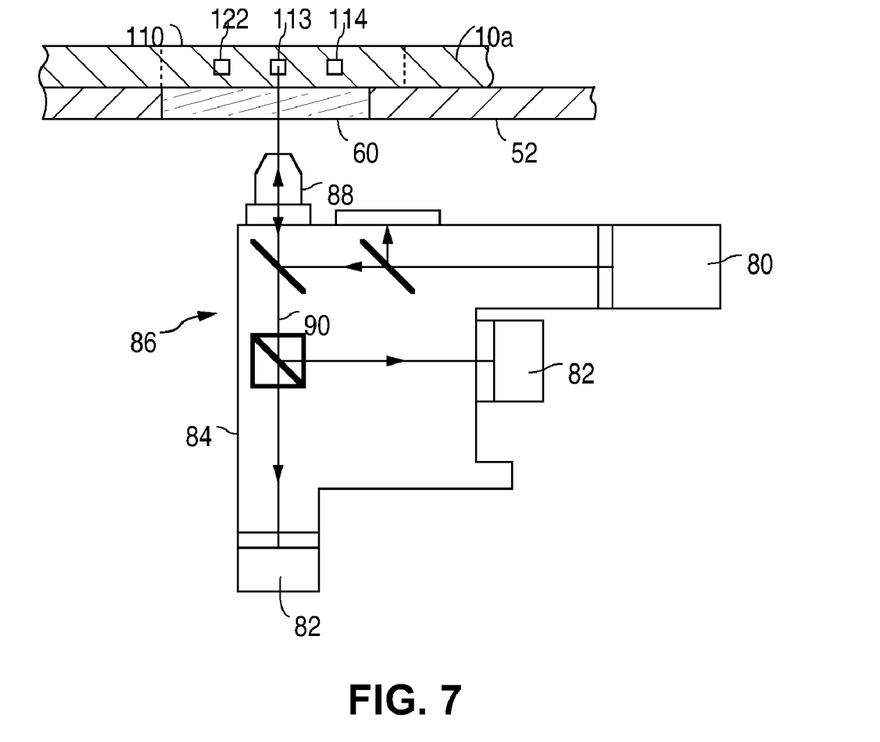
FIG. 7 is a partial sectional view of the instrument of FIG. 6, showing the projection and detection of light with respect to the device of FIG. 2 located thereon.

Referring now to FIG. 7, there is shown a light source 80 and a detector 82 in schematic form, held within a housing 84. The embodiment of FIG. 7 may be employed when the detectable signal produced by the indicator is a fluorescent signal. Preferably, the light source 80 is a laser or laser diode, having the light emitted therefrom directed through a system of mirrors and optics 86, to and through a lens 88 locatable immediately below window 60 of base 52. The light beam, as shown by heavy line 90, is positionable to pass into one of the channels, for example channel 113 in the detection region 110 of microfluidic device 10a. When a fluorescent signal is produced by an indicator as a result of the indicator being illuminated with a wavelength of light that excites the fluorescence, the resulting light will enter lens 88 and be directed by the mirrors and optics 86 to one or more detectors 82. The detector(s) 82, mirrors and optics 86, lens 88 and light source 80 are all preferably housed in housing 84, which housing is moveable in x, y and z directions through the use of a plurality of servo motors and lead screw arrangements (not shown). Thus, when a microfluidic device 10a is positioned on base 52, the device 10a remains stationary, and the housing 84 moves under base 52 to position the lens 88 to direct the light beam through discrete ones of the channels in the detection region 110 of the device 10a. By focusing the light beam 90 onto only one channel in the detection region 110, cross talk from fluorescent signals from other channels is minimized. The positioning and control of the housing 84 and light source are well known to one skilled in the art, and the controller can be preprogrammed to bring the housing to a pre-selected zero point, and then move the housing 84 to a series of pre-selected positions, based upon a pre-programmed script based on the known locations of the channels in the detection region 110 of the microfluidic device 10a.

Figure 8:
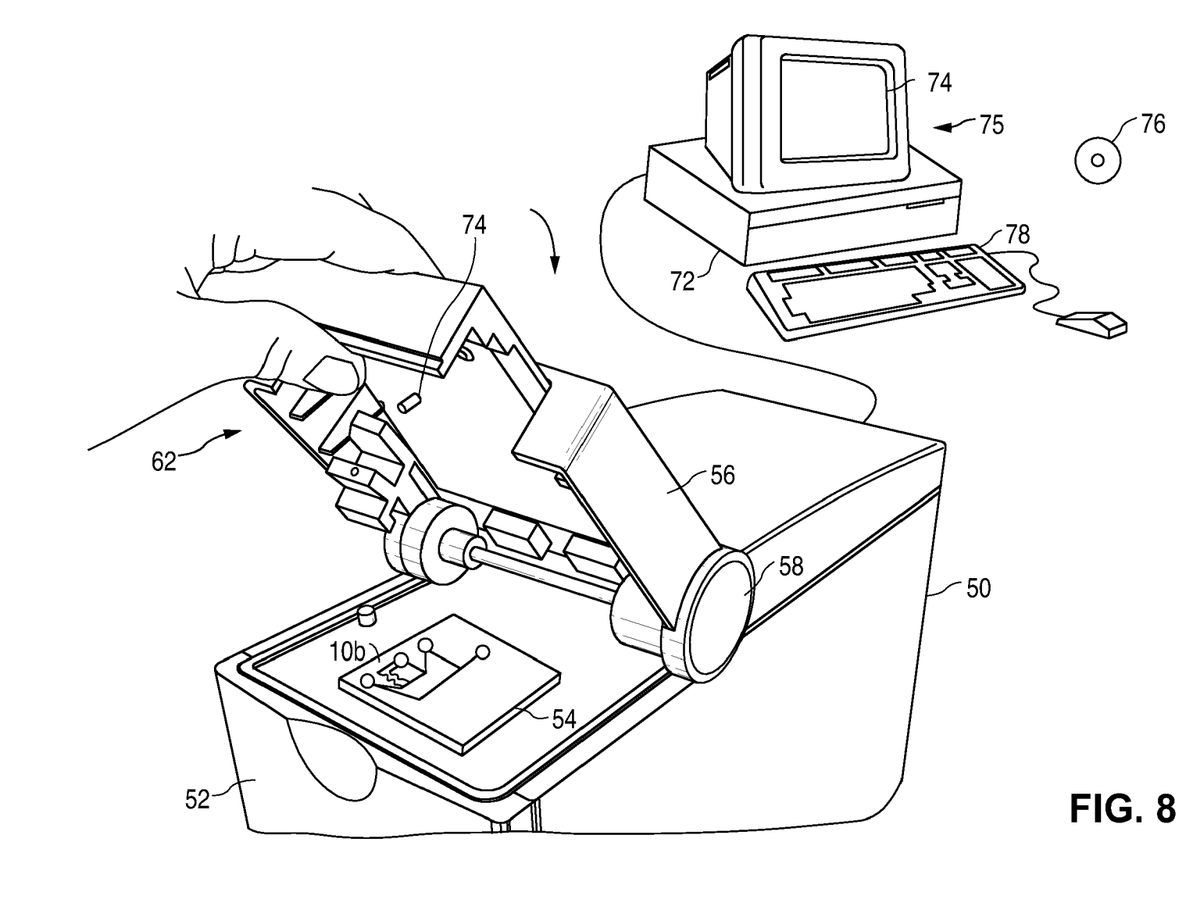
FIG. 8 is a partial perspective view of an instrument for practicing the present invention in conjunction with the devices shown in FIGS. 3 to 5.

Referring now to FIG. 8, there is shown an alternative instrument structure, wherein the plurality of lumens in FIG. 6 have been replaced by a single vacuum port 74. The embodiment of FIG. 8 is compatible with embodiments employing single vacuum source control systems, while the embodiment of FIG. 6 is compatible with embodiments employing multiport control systems. When cover 56 in FIG. 8 is closed; the single vacuum port 74 is received in sealing engagement with waste well 112 of microfluidic device 10b. To carry out an analysis, a vacuum pressure is applied to the waste well on device 10b, causing fluids in the remaining wells to flow into the channels of the device 10b.

III. Examples

A. Analysis using the Microfluidic Device of FIG. 2

Embodiments of the present invention may be used to successfully, accurately, and repeatably determine the concentration of materials of interest in fluid samples collected from industrial processes. For example, the fluid samples may be hydrocarbon exploration samples, namely drilling mud. To prepare a sample of drilling mud for analysis in the microfluidic device 10 of FIG. 2: the sample is recovered from the drilling mud being used to drill a borehole into the earth, and the sample is passed through a filter to remove any solids therein which would interfere with the free flow of the fluid sample through the microfluidic device. Preferably, the filter has a pore size in the range of 0.2 μm, resulting in a maximum sample particulate size smaller than 0.2 μm. The sample is then diluted to a dilution ratio of one part sample to about five parts to two hundred parts (by volume) of a buffer material having a pH of 7.5 to make up a diluted sample for placement in a reservoir of microfluidic device 10. By combining the sample with a large quantity of pH 7.5 buffer, the resulting diluted sample will have a pH of 7.5 irrespective of its starting pH. Thus, the pH of the diluted sample is known, so an indicator that operates at that pH can be employed in the analysis. The concentration of the material of interest in the sample should be within, or close to, the dynamic range of the indicator used in the analysis. This can be accomplished if an even approximate concentration of the material of interest is known. Otherwise, the proper level of dilution may have to be determined by trial and error.

Once the diluted sample is prepared, the microfluidic device 10 is loaded with the appropriate samples, indicators, and buffers. To load the device 10, a five microliter volume of diluted sample is drawn by a technician with a pipette, and then placed into sample well 16. Likewise five microliters of a reference sample is deposited into reference sample well 12, and five microliters of buffer is placed into buffer wells 14 and 18, and five microliters of each indicator is placed into the first and second indicator wells 20, 22. For example, to analyze the sample for the presence of calcium and chloride, a chloride-sensitive indicator such as lucigenin is loaded into indicator well 20, and a calcium-sensitive indicator such as Fura FF or Mag Fura is loaded into indicator well 22. These indicators are available from Molecular Probes of Eugene, Oreg. The device 10 is then placed into instrument 50 of FIG. 6, the cover plate 56 brought into the closed position on base 52, and pressure is selectively applied to the wells 12 to 22 through lumens 64 to push the fluids through the channels and through the detection region 28. Once the time necessary to ensure mixing of the fluids and the presence of the first of these to reach the detection region 28 of device 10 has passed, the light beam illuminates main channel 32 therein to enable fluorescence and a detection of the intensity of fluorescence of the materials passing through the detection region 28. It should be noted that the combinations of sample and indicator would be mixed as they travel through channel 32 before they reach the detection region 28. The pressures applied at the separate wells enables multiple dilutions of control sample fluid and sample fluid in the buffer and indicator to be prepared on the device for analysis thereon.

B. Analysis Using the Devices of FIGS. 3 to 5

A similar methodology is used with microfluidic devices that interface with single vacuum source control systems, such as devices 10a, 10b and 10c in FIGS. 3, 4, and 5. As in the previous example, the fluid samples may be hydrocarbon exploration samples such as drilling mud. Just as in the previous example, a raw sample must be filtered and diluted before it is placed within the microfluidic device for analysis. If the sample is diluted so that the concentration of the material of interest is within the dynamic range of the indicator, the simple device 10b from FIG. 4 can be used. If the material of interest is calcium or chloride, then one of the appropriate indicators described in the previous example could be used. To use device 10b from FIG. 4, five microliters of a diluted sample is pipetted into sample well 102, five microliters of reference sample is pipetted into reference sample well 108, and five microliters of indicator solution are pipetted into indicator well 106. As noted above, the microfluidic device 10b must have been previously primed. The device 10b is placed into the instrument 50 of FIG. 8, and vacuum is applied to waste well 112 through vacuum port 74, causing reference samples, the sample of unknown concentration, and indicator to flow into their respective channels. The mixtures of sample and indicator pass through detection region 110 where they are illuminated, producing a detectable fluorescence.

Although the two examples involve samples from hydrocarbon exploration, those skilled in the art will recognize the vast number and types of applications to which embodiments of the invention are well suited. Generally, embodiments of the invention are useful for monitoring the presence of and determining the concentration of material present in fluids from industrial processes. For example, environmental regulations limit the amount of chlorides, calcium, etc., that may be present upon disposal of fluids from industrial processes. Embodiments of the present invention are readily applicable to the analysis of such fluids, and the results of analysis will enable an operator to certify that the fluid is properly dischargeable. In industrial processing, such as where a food product such as pasteurized processed cheese food is manufactured, certain constituents of the product are frequently monitored, to ensure the production of a useable food product. The present invention provides a non-operator dependent, rapid, capability for such analysis, with rapid feedback to adjust the input stocks to the product, as well as the capability to verify and store, in memory for later retrieval should a dispute arise as to the quality or constituents of the food product, the results of analysis as well as the time of analysis. Likewise, in industrial operations where fluids and other materials are repeatedly used in operations, and must be disposed of or periodically monitored and supplemented with necessary materials, the present invention provides great advantage over prior art manual methods. In chemical plants, where heat exchanging fluids are cooled and recycled through heat exchangers, the invention can be used to analyze the constituents of the cooling medium and indicate adjustments to the coolant chemistry to reduce fouling, rust and scale formation, etc. Finally, the invention may also be used to simply provide an indication of the mere presence of a constituent in a process flow, particularly where the constituent is detrimental to the process.

All publications and patent documents cited in this application are incorporated by reference in their entirety for all purposes to the same extent as if each individual publication or patent document were so individually denoted. While the foregoing is directed to embodiments of the present invention, other and further embodiments of the invention may be devised without departing from the basic scope thereof, and the scope thereof is determined by the claims that follow.

I claim:

1. A method of determining unknown concentrations of an inorganic ion of interest in a recovered sample comprising the steps of:

providing a microfluidic device comprising a sample well having the recovered sample disposed therein, an indicator well having a fluorescent indicator disposed therein, a control well having a control disposed therein, the control including a known quantity of the inorganic ion of interest, a waste well, a detection region, and a light source directed at the detection region;

wherein the sample well, the indicator well, and the waste well form a first fluidic circuit, the sample well fluidly coupled to the waste well via a first channel, and the indicator well fluidly connected to the first channel via a second channel;

and wherein the indicator well, the control well, and the waste well form a second fluidic circuit, the indicator well fluidly coupled to the waste well via a third channel, and the control well fluidly coupled to the third channel via fourth, fifth, and sixth channels, each of the fourth, fifth, and sixth channels having a different flow resistance;

mixing, in the third channel, the control sample and the fluorescent indicator, wherein flowing the control sample into the third channel via the fourth, fifth, and sixth channels provides a plurality of relative known ratios of the control sample in the indicator;

obtaining a signal representative of the concentration of the inorganic ion of interest in each of the ratios, wherein the signal comprises an intensity of fluorescence;

generating a model representative of the signal and the relative ratio of the control sample in the indicator;

mixing, in the first channel, the recovered sample and the fluorescent indicator, and obtaining a signal representative of the concentration of the inorganic ion of interest therein, wherein the signal comprises an intensity of fluorescence; and comparing the signal representative of the inorganic ion of interest for the recovered sample within the model, thereby providing a determination of the concentration of the inorganic ion of interest present in the recovered sample.

2. The method of claim 1, wherein the signal indicative of the inorganic ion of interest concentration is an intensity of fluorescence, and the model is a graphical representation of the fluorescence intensity vs. concentration of the inorganic ion of interest.

3. The method of claim 1 wherein the microfluidic device further comprises a buffer well having a buffer disposed therein, the buffer well, the sample well, the indicator well, and the waste well forming a third fluidic circuit, the sample well further fluidly coupled to the waste well via a seventh channel, the buffer well fluidly coupled to the seventh channel via an eighth channel, and the indicator well further fluidly connected to the seventh channel via a ninth channel, the method further including the step of mixing, in the seventh channel, a combination of recovered sample, buffer, and fluorescent indicator and passing the combination through the detection region for analysis.

4. The method of claim 1 wherein the microfluidic device further comprises a second sample well having a second recovered sample disposed therein, the second sample well, the indicator well, and the waste well forming a fourth fluidic circuit, the second sample well fluidly coupled to the waste well via a tenth channel, and the indicator well further fluidly connected to the tenth channel via an eleventh channel, the method further including the steps of:

flowing the second recovered sample from the second sample well;

mixing, in the tenth channel, the second recovered sample with the buffer and the fluorescent indicator; and obtaining a signal indicative of the concentration of an inorganic ion of interest in this mixture, wherein the signal comprises an intensity of fluorescence.

5. The method of claim 1, wherein pressure is applied to at least one well of the device to cause each of the mixing steps.

6. The method of claim 5, wherein the pressure is a vacuum.

7. The method of claim 5, wherein the pressure is above atmospheric.

* * * * *